United States Patent
Reihani et al.

(10) Patent No.: US 10,253,367 B1
(45) Date of Patent: Apr. 9, 2019

(54) BIOMARKERS FOR LOCALLY ADVANCED BREAST CANCER (LABC) AND INFLAMMATORY BREAST CANCER (IBC)

(71) Applicant: Duke University, Durham, NC (US)

(72) Inventors: Sharareh Reihani, Chapel Hill, NC (US); Mark Dewhirst, Chapel Hill, NC (US); Kouros Owzar, Chapel Hill, NC (US); Oana Craciunescu, Hillsborough, NC (US)

(73) Assignee: DUKE UNIVERSITY, Durham, NC (US)

( * ) Notice: Subject to any disclaimer, the term of this patent is extended or adjusted under 35 U.S.C. 154(b) by 53 days.

(21) Appl. No.: 14/176,999

(22) Filed: Feb. 10, 2014

Related U.S. Application Data

(60) Provisional application No. 61/762,511, filed on Feb. 8, 2013.

(51) Int. Cl.
  *C12Q 1/68*  (2018.01)
  *C12Q 1/6886*  (2018.01)

(52) U.S. Cl.
  CPC .................... *C12Q 1/6886* (2013.01)

(58) Field of Classification Search
  None
  See application file for complete search history.

(56) References Cited

PUBLICATIONS

Dressman et al; Clinical Cancer Research, vol. 12, pp. 819-826, 2006.*

* cited by examiner

*Primary Examiner* — Jehanne S Sitton
(74) *Attorney, Agent, or Firm* — NK Patent Law

(57) ABSTRACT

The present disclosure provides methods and kits for using biomarkers for predicting treatment response, determining likely survival rate, and/or determining aggressiveness of conditions such as Locally Advanced Breast Cancer (LABC) and Inflammatory Breast Cancer (IBC) in a subject.

8 Claims, 4 Drawing Sheets

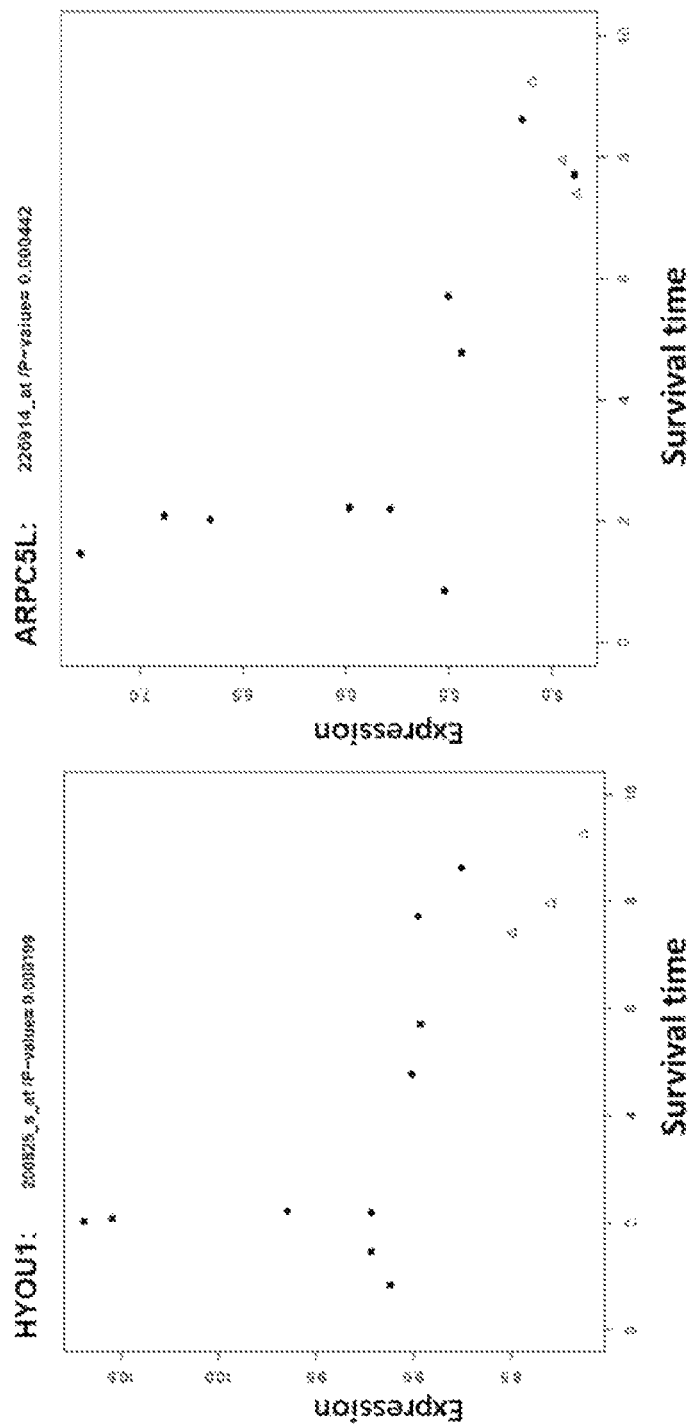

BIOMARKERS FOR LOCALLY ADVANCED BREAST CANCER (LABC) AND INFLAMMATORY BREAST CANCER (IBC)

CROSS REFERENCE TO RELATED APPLICATIONS

This application claims the benefit of U.S. provisional patent application No. 61/762,511, filed Feb. 8, 2013, the disclosure of which is hereby incorporated by reference in its entirety.

FEDERAL FUNDING LEGEND

The invention was made with government support under Grant No.'s 5R01 CA40355-27 and 5P01 CA42745-23 awarded by the National Institute of Health. The government has certain rights in the invention.

TECHNICAL FIELD

The presently disclosed subject matter relates to methods and kits for using biomarkers to predict treatment response, determine likely survival rate, and/or determine aggressiveness of Locally Advanced Breast Cancer (LABC) and Inflammatory Breast Cancer (IBC).

BACKGROUND

Locally advanced breast cancer (LABC) and inflammatory breast cancer (IBC) have poor 5-year survival rates (55% and 33%, respectively), compared to early-stage breast cancer (80%). [1-3] Prior to surgery, neoadjuvant chemotherapy is used to down-stage patients with locally advanced breast cancer (LABC) and inflammatory breast cancer (IBC), a subset of LABC. The rationale for downstaging the tumor before surgery is that it will provide the option for a more conservative surgery and can even change an inoperable tumor to an operable one in some cases.[4] However, not all patients respond equally well to the neoadjuvant treatment and effective biomarkers that can predict treatment response are lacking. Patients who achieve a pathologic clinical response (pCR) have a better prognosis, but there is a need for effective biomarkers to predict which patients will achieve pCR.

It has been previously reported that DCE-MRI parameters are linked to treatment outcome in canine and human cancers.[5,16] This was the first study to report a linkage between DCE-MRI parameters in sarcomas and long-term outcome.[16] In humans, it has been previously reported that DCE-MRI perfusion patterns, obtained from LABC patients prior to neoadjuvant therapy, were predictive of pathologic clinical response.[5] Genomic analyses were also independently conducted on the same patient LABC population.[6]

Thus, there is an umet need for biomarkers for breast cancer, and the present disclosure provides such biomarkers.

SUMMARY OF THE DISCLOSURE

In one embodiment of the presently disclosed subject matter, a method is provided for predicting locally advanced breast cancer (LABC) treatment response, the method comprising: quantifying the amount of one or more biomarkers for LABC present in a biological sample derived from a subject, wherein the biomarker comprises one or a combination of SULT1A1, SULT1A2, PARP6, and MTA1; and predicting the subject as having an increased chance of benefiting from a chemotherapeutic treatment if the amount of the biomarker is higher in the biological sample derived from the subject as compared to a reference control.

In one embodiment of the presently disclosed subject matter, a method is provided for determining likely survival rate for Inflamatory Breast Cancer (IBC), the method comprising: quantifying the amount of one or more biomarkers for IBC present in a biological sample derived from a subject, wherein the biomarker comprises one or a combination of ARPC5L, HYOU1, AVEN, CHST11, TLN2, CHST3, PRKCA, COL4A4, and TNC; and predicting the subject as having an increased chance of survival if the amount of the biomarker is decreased in the biological sample derived from the subject as compared to a reference control.

In one embodiment of the presently disclosed subject matter, a method is provided for determining the aggressiveness of locally advanced breast cancer (LABC) in a subject, the method comprising: quantifying the amount of a MTA1 biomarker present in a biological sample derived from the subject, wherein the subject exhibited a centrifugal (CF) enhancement pattern as measured by dynamic contrast-enhanced magnetic resonance imaging (DCE-MRI); and predicting the subject as having a more aggressive cancer if the MTA1 biomarker is increased in the biological sample derived from the subject as compared to a reference control.

In one embodiment of the presently disclosed subject matter, a kit is provided for predicting breast cancer treatment response, the kit comprising: a probe for quantifying the amount of one or more biomarkers for locally advanced breast cancer (LABC) present in a biological sample derived from a subject, wherein the biomarker comprises one or a combination of SULT1A1, SULT1A2, and PARP6, and MTA1; and instructions for quantifying the amount of the biomarker in the biological sample and for predicting the subject as having an increased chance of benefiting from a chemotherapeutic treatment if the amount of the biomarker is higher in the biological sample derived from the subject compared to a reference control.

In one embodiment of the presently disclosed subject matter, a kit is provided for determining likely survival rate for Inflammatory Breast Cancer (IBC), the kit comprising: a probe for quantifying the amount of one or more biomarkers for IBC present in a biological sample derived from a subject, wherein the biomarker comprises one or a combination of ARPC5L, HYOU1, AVEN, CHST11, TLN2, CHST3, PRKCA, COL4A4, and TNC; and instructions for quantifying the amount of the biomarker in the biological sample and for predicting the subject as having an increased chance of survival if the biomarker is decreased in the biological sample derived from the subject as compared to a reference control.

In one embodiment of the presently disclosed subject matter, a kit is provided for determining the aggressiveness of locally advanced breast cancer (LABC) in a subject, the kit comprising: a probe for quantifying the amount of a MTA1 biomarker present in a biological sample derived from the subject, wherein the subject exhibited a centrifugal (CF) enhancement pattern as measured by dynamic contrast-enhanced magnetic resonance imaging (DCE-MRI); and instructions for quantifying the amount of the MTA1 biomarker in the biological sample and for predicting the subject as having a more aggressive cancer if the MTA1 biomarker is increased in the biological sample derived from the subject as compared to a reference control.

The present disclosure provides methods of determining the aggressiveness of a breast cancer in a subject and/or determining the likelihood of survival in a subject suffering from breast cancer comprising, consisting of, or consisting essentially of quantifying the amount of at least one biomarker present in a biological sample derived from the subject, wherein the biomarker comprises, consists of, or consists essentially of a protein associated with breast cancer aggressiveness and/or likelihood of survival.

One aspect of the present disclosure provides a method of determining the aggressiveness of a breast cancer in a subject comprising quantifying the amount of at least one biomarker present in a biological sample derived from the subject, wherein the biomarker is associated with breast cancer aggressiveness.

Another aspect of the present disclosure provides a method of predicting the likely survival rate of a subject suffering from breast cancer comprising quantifying the amount of at least one biomarker present in a biological sample derived from the subject, wherein the biomarker is associated with patient survival.

Another aspect of the present disclosure provides a method of determining the aggressiveness of a breast cancer in a subject comprising: (a) obtaining a biological sample from a subject; (b) determining the expression level of one or more biomarkers that are associated with breast cancer aggressiveness in the biological sample; (c) comparing the expression level of the biomarkers in the biological sample with that of a control, wherein the presence of one or more of the biomarkers in the sample that is in an amount greater than that of the control indicates the breast cancer is not aggressive; and (d) administering appropriate breast cancer therapy if one or more of the biomarkers are expressed.

Another aspect of the present disclosure provides a method of determining the aggressiveness of a breast cancer of a subject comprising: (a) obtaining a biological sample from a subject; (b) determining the expression level of one or more biomarkers that are associated with breast cancer aggressiveness in the biological sample; (c) comparing the expression level of the biomarkers in the biological sample with that of a control, wherein the presence of one or more of the biomarkers in the sample that is in an amount greater than that of the control indicates the breast cancer is aggressive; and (d) administering an appropriate breast cancer therapy if one or more of the biomarkers are expressed.

Yet another aspect of the present disclosure provides a method of predicting the likely survival rate of a subject suffering from breast cancer comprising: (a) obtaining a biological sample from a subject; (b) determining the expression level of one or more biomarkers that are associated with breast cancer survival in the biological sample; (c) comparing the expression level of the biomarkers in the biological sample with that of a control, wherein the presence of one or more of the biomarkers in the sample that is in an amount less than that of the control indicates a greater likelihood of survival; and (d) administering an appropriate breast cancer therapy if one or more of the biomarkers are expressed.

In some embodiments, the biomarker comprises, consists of, or consists essentially of a protein, a phosphoprotein, nucleic acid, peptide or combinations thereof. In certain embodiments, the biomarker comprises a protein. In some embodiments, the biomarker is a protein selected from the group consisting of SULTIA1, SULTIA2, MTA1 and combinations thereof. In other embodiments, the biomarker is a protein selected from the group consisting of HYOU1, ARPC5L, AVEN and combinations thereof. In other embodiments, the biomarker is a protein selected from the group consisting of SULTIA1, SULTIA2, and combinations thereof. In yet another embodiment, the biomarker comprises MTA1.

Another aspect of the present disclosure provides a composition of matter comprising: (a) a probe array for determining a biomarker level in a sample, the array comprising of a plurality of probes that hybridizes to one or more biomarkers that are associated with breast cancer aggressiveness and/or likelihood of breast cancer survival; or (b) a kit for determining a biomarker level in a sample, comprising the probe array of (a) and instructions for carrying out the determination of biomarker expression level in the sample.

In some embodiments, the probe array of (a) further comprises a solid support with the plurality of probes attached thereto.

In some embodiments, the subject is a mammal. In other embodiments, the subject is a human.

In other embodiments, the biological sample is selected from the group consisting of tissues, cells, biopsies, blood, lymph, serum, plasma, urine, saliva, mucus, and tears. In certain embodiments, the sample comprises cells.

BRIEF DESCRIPTION OF THE DRAWINGS

The foregoing aspects and other features of the disclosure are explained in the following description, taken in connection with the accompanying drawings, wherein:

FIGS. 3A & 3B are graphs showing differential gene expression of HYOU1 (A) and ARPC5L (B) in relation to patient survival time according to one or more embodiments of the present disclosure. "Survival Time" unit is in years. Three of the patients who were still alive at the time of the data analysis are represented with a "triangle" symbol.

DETAILED DESCRIPTION OF THE DISCLOSURE

Figure 1A:
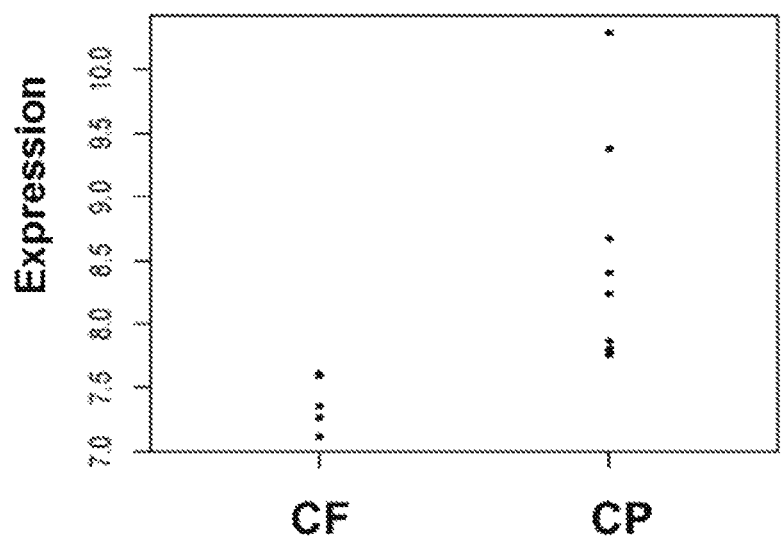
FIGS. 1A & 1B are graphs showing differential gene expression of the sulfotransferases SULTIA1 (A) and SULTIA2 (B) in centripetal (CP) and centrifugal (CF) locally advanced breast cancer (LABC) samples according to one or more embodiments of the present disclosure.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

DEFINITIONS

As used herein, the term "biomarker" refers to a naturally occurring biological molecule present in a subject at varying concentrations useful in predicting the risk or incidence of a disease, the aggressiveness of a disease or a condition, or the likelihood of surviving a disease or condition, such as breast cancer. For example, the biomarker can be a protein present in higher or lower amounts in a subject as compared to a control that indicates the aggressiveness of a disease/condition or likelihood of survival of said disease/condition. The biomarker can include proteins, phosphopeptides, nucleic acids, ribonucleic acids, etc. and combinations thereof used as an indicator or marker for breast cancer aggressiveness and/or survivability in a subject. In some embodiments, the biomarker comprises a protein.

In one embodiment, the biomarker(s) associated with less aggressive breast cancer comprise, consist of, or consist essentially of one or more of the following proteins: SULTIA1, SULTIA2 and combinations thereof.

In another embodiment, the biomarker(s) associated with aggressive breast cancer may comprise, consist of, or consist essentially of MTA1.

In another embodiment, the biomarker(s) associated with survivability may comprise, consist of, or consist essentially of one or more of the following proteins: HYOU1, ARPC5L, AVEN and combinations thereof.

As used herein, the term "breast cancer" refers to those types of cancers that origin at from the breast tissue, most commonly from the inner lining of milk ducts or the lobules that supply the ducts with milk.

"About" is used to provide flexibility to a numerical range endpoint by providing that a given value may be "slightly above" or "slightly below" the endpoint without affecting the desired result.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. For example, such therapies may include surgery, medications (hormonal therapy and/or chemotherapy), radiation, immunotherapy and the like. Such treatments are well known and particular to the patient and can be readily determined by one skilled in the art.

The term "effective amount" or "therapeutically effective amount" refers to an amount sufficient to effect beneficial or desirable biological and/or clinical results.

DETAILED DESCRIPTION

The present disclosure provides biomarkers useful for determining the aggressiveness of a breast cancer in a subject and/or the likelihood of survival for a subject suffering from breast cancer.

Advantageously, the methods of the present disclosure are noninvasive, highly specific, and sensitive.

In one embodiment, the present disclosure profiles biomarkers found in biological samples (e.g., tissues, cells, plasma and the like) for determining the aggressiveness of a breast cancer in a subject and/or the likelihood of survival for a subject suffering from breast cancer.

In one embodiment, the present disclosure identifies plasma protein profiles as biomarkers for determining the aggressiveness of a breast cancer in a subject and/or the likelihood of survival for a subject suffering from breast cancer. The inventors have determined that certain biomarkers are directly involved in breast cancer aggressiveness and/or likelihood of survival, and their expression pattern in a biological sample can be associated with the pathophysiological status of the subject suffering from breast cancer.

One aspect of the present disclosure provides biomarkers useful for determining the aggressiveness of a breast cancer in a subject In one embodiment, the present disclosure provides biomarkers that are differentially expressed, such as upregulated, down-regulated, or disregulated in a condition such as breast cancer, as compared to normal populations who do not have the condition, such as breast cancer.

In some embodiments, the biomarker comprises a protein. In one embodiment, the biomarker(s) associated with non- or less-aggressive breast cancer comprise, consist of, or consist essentially of one or more of the following proteins: SULTIA1, SULTIA2 and combinations thereof.

In another embodiment, the biomarker(s) associated with aggressive breast cancer may comprise, consist of, of consist essentially of the protein MTA1.

In another embodiment, the biomarker(s) associated with likelihood of survival from breast cancer may comprise, consist of, or consist essentially of one or more of the following proteins: HYOU1, ARPC5L, AVEN and combinations thereof.

In some embodiments, these biomarkers are up-regulated or over-expressed, or down-regulated or under-expressed, more than 50-fold, 40-fold, 30-fold, 20-fold, 15-fold, 10-fold, 9-fold, 8-fold, 7-fold, 6-fold, 5-fold, 4-fold, 3-fold, 2-fold, or 1-fold in a subject at, when compared to a control.

In one embodiment, the present disclosure provides a method for determining the aggressiveness of a breast cancer in a subject comprising, consisting of, or consisting essentially of: (a) determining a biomarker expression profile (expression level) in a biological sample from the subject; (b) characterizing the subject's biomarker profile; and (c) comparing the subject's biomarker profile with the biomarker profile of a control from subjects not at risk of breast cancer; and (d) administering an appropriate breast cancer therapy if one or more of the biomarkers are expressed.

In another embodiment, the present disclosure provides a method for determining the likelihood of survival of a subject suffering from breast cancer comprising, consisting of, or consisting essentially of: (a) determining a biomarker expression profile (expression level) in a biological sample from the subject; (b) characterizing the subject's biomarker profile; and (c) comparing the subject's biomarker profile with the biomarker profile of a control profile from subjects not at risk of breast cancer; and (d) administering an appropriate breast cancer therapy if one or more of the biomarkers are expressed.

In one embodiment, the method further includes obtaining the biological sample from the subject. In one embodiment, the determination of the aggressiveness of a breast cancer and/or the likelihood of survival of a person suffering from breast cancer can be determined by comparing the subjects biomarker profile to a reference biomarker profile, such as one that corresponds to biological samples obtained from a normal population that do not have a condition such as breast cancer, or that corresponds to biological samples obtained from a population that have a condition such as breast cancer. Optionally, the reference profile comprises multiple biomarker expression profiles, with each corresponding to a different stage of a condition such as breast cancer.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. Preferably, the subject is a human patient that is at for, or suffering from, breast cancer.

The term "biological sample" as used herein includes, but is not limited to, a sample containing tissues, cells, and/or biological fluids isolated from a subject. Examples of biological samples include, but are not limited to, tissues, cells, biopsies, blood, lymph, serum, plasma, urine, saliva, mucus and tears. In one embodiment, the biological sample is a blood sample (such as a plasma sample) or biopsy sample (such as a tissue/cell sample). A biological sample may be obtained directly from a subject (e.g., by blood or tissue sampling) or from a third party (e.g., received from an intermediary, such as a healthcare provider or lab technician).

In one embodiment of the presently disclosed subject matter, a method is provided for predicting locally advanced breast cancer (LABC) treatment response, the method comprising: quantifying the amount of one or more biomarkers for LABC present in a biological sample derived from a subject, wherein the biomarker comprises one or a combination of SULT1A1, SULT1A2, PARP6, and MTA1; and predicting the subject as having an increased chance of benefiting from a chemotherapeutic treatment if the amount of the biomarker is higher in the biological sample derived from the subject as compared to a reference control.

In the method for predicting LABC treatment response, the biomarker can comprise SULT1A1, SULT1A2, and PARP6 and the subject can exhibit a centripetal (CP) enhancement pattern as measured by dynamic contrast-enhanced magnetic resonance imaging (DCE-MRI). The biomarker can comprise MTA1 and the subject can exhibit a centrifugal (CF) enhancement pattern as measured by dynamic contrast-enhanced magnetic resonance imaging (DCE-MRI).

In the method for predicting LABC treatment response, the amount of the biomarker can be a gene expression level. The biomarker can comprise a nucleic acid, protein, phosphoprotein, peptide or combinations thereof.

In the method for predicting LABC treatment response, the biological sample can comprise tissues, cells, biopsies, blood, lymph, serum, plasma, urine, saliva, mucus, tears, and combinations thereof. The biological sample can comprise cells.

In the method for predicting LABC treatment response, the subject can be a mammal. The subject can be a human.

In the method for predicting LABC treatment response, the method can further comprise administering the chemotherapeutic treatment to the subject.

In one embodiment of the presently disclosed subject matter, a method is provided for determining likely survival rate for Inflamatory Breast Cancer (IBC), the method comprising: quantifying the amount of one or more biomarkers for IBC present in a biological sample derived from a subject, wherein the biomarker comprises one or a combination of ARPC5L, HYOU1, AVEN, CHST11, TLN2, CHST3, PRKCA, COL4A4, and TNC; and predicting the subject as having an increased chance of survival if the amount of the biomarker is decreased in the biological sample derived from the subject as compared to a reference control.

In the method for determining likely survival rate for IBC, the amount of the biomarker can be a gene expression level. The biomarker can comprise a nucleic acid, protein, phosphoprotein, peptide or combinations thereof.

In the method for determining likely survival rate for IBC, the biological sample can comprise tissues, cells, biopsies, blood, lymph, serum, plasma, urine, saliva, mucus, tears, and combinations thereof. The biological sample can comprise cells.

In the method for determining likely survival rate for IBC, the subject can be a mammal. The subject can be a human.

In the method for determining likely survival rate for IBC, the method can further comprise administering an appropriate treatment to the subject based on the prediction.

In one embodiment of the presently disclosed subject matter, a method is provided for determining the aggressiveness of locally advanced breast cancer (LABC) in a subject, the method comprising: quantifying the amount of a MTA1 biomarker present in a biological sample derived from the subject, wherein the subject exhibited a centrifugal (CF) enhancement pattern as measured by dynamic contrast-enhanced magnetic resonance imaging (DCE-MRI); and predicting the subject as having a more aggressive cancer if the MTA1 biomarker is increased in the biological sample derived from the subject as compared to a reference control.

In the method for determining the aggressiveness of LABC in a subject, the amount of the MTA1 biomarker can be a gene expression level. The MTA1 biomarker can comprise a nucleic acid, protein, phosphoprotein, peptide or combinations thereof.

In the method for determining the aggressiveness of LABC in a subject, the biological sample can comprise tissues, cells, biopsies, blood, lymph, serum, plasma, urine, saliva, mucus, tears, and combinations thereof. The biological sample can comprise cells.

In the method for determining the aggressiveness of LABC in a subject, the subject can be a mammal. The subject can be a human.

In the method for determining the aggressiveness of LABC in a subject, the method can further comprise administering an appropriate treatment to the subject based on the prediction.

In one embodiment of the presently disclosed subject matter, a kit is provided for predicting breast cancer treatment response, the kit comprising: a probe for quantifying the amount of one or more biomarkers for locally advanced breast cancer (LABC) present in a biological sample derived from a subject, wherein the biomarker comprises one or a combination of SULT1A1, SULT1A2, and PARP6, and MTA1; and instructions for quantifying the amount of the biomarker in the biological sample and for predicting the subject as having an increased chance of benefiting from a chemotherapeutic treatment if the amount of the biomarker is higher in the biological sample derived from the subject compared to a reference control.

In the kit for predicting breast cancer treatment response, the biomarker can be a nucleic acid and the probe can comprise a nucleic acid specific for hybridization to the nucleic acid biomarker. The quantifying the amount of the biomarker can be carried out by one or a combination of Polymerase Chain Reaction, Real Time-Polymerase Chain Reaction, Real Time Reverse Transcriptase-Polymerase Chain Reaction, Northern blot analysis, in situ hybridization, and Array system.

In the kit for predicting breast cancer treatment response, the probe can be attached to a solid support.

In the kit for predicting breast cancer treatment response, the kit can further comprise reagents for determining the level of the biomarker.

In the kit for predicting breast cancer treatment response, the biomarker can be a polypeptide and the probe can comprise an antibody or a binding fragment specific for the polypeptide. The quantifying the amount of biomarker can be carried out by an assay comprising one or a combination of Western Blotting, affinity matrice, and immunoassay.

In the kit for predicting breast cancer treatment response, the amount of the biomarker can be a gene expression level.

In the kit for predicting breast cancer treatment response, the biological sample can comprise tissues, cells, biopsies, blood, lymph, serum, plasma, urine, saliva, mucus, tears, and combinations thereof. The biological sample can comprise cells.

In the kit for predicting breast cancer treatment response, the subject can be a mammal. The subject can be a human.

In one embodiment of the presently disclosed subject matter, a kit is provided for determining likely survival rate for Inflammatory Breast Cancer (IBC), the kit comprising: a probe for quantifying the amount of one or more biomarkers for IBC present in a biological sample derived from a subject, wherein the biomarker comprises one or a combination of ARPC5L, HYOU1, AVEN, CHST11, TLN2, CHST3, PRKCA, COL4A4, and TNC; and instructions for quantifying the amount of the biomarker in the biological sample and for predicting the subject as having an increased chance of survival if the biomarker is decreased in the biological sample derived from the subject as compared to a reference control.

In the kit for determining likely survival rate for IBC, the biomarker can be a nucleic acid and the probe can comprise a nucleic acid specific for hybridization to the nucleic acid biomarker. The quantifying the amount of the biomarker can be carried out by one or a combination of Polymerase Chain Reaction, Real Time-Polymerase Chain Reaction, Real Time Reverse Transcriptase-Polymerase Chain Reaction, Northern blot analysis, in situ hybridization, and Array system. The probe can be attached to a solid support.

In the kit for determining likely survival rate for IBC, the kit can further comprise reagents for determining the level of the biomarker.

In the kit for determining likely survival rate for IBC, the biomarker can be a polypeptide and the probe can comprise an antibody or a binding fragment specific for the polypeptide. The quantifying the amount of biomarker can be carried out by an assay comprising one or a combination of Western Blotting, affinity matrice, and immunoassay.

In the kit for determining likely survival rate for IBC, the amount of the biomarker can be a gene expression level.

In the kit for determining likely survival rate for IBC, the biological sample can comprise tissues, cells, biopsies, blood, lymph, serum, plasma, urine, saliva, mucus, tears, and combinations thereof. The biological sample can comprise cells.

In the kit for determining likely survival rate for IBC, the subject can be a mammal. The subject can be a human.

In one embodiment of the presently disclosed subject matter, a kit is provided for determining the aggressiveness of locally advanced breast cancer (LABC) in a subject, the kit comprising: a probe for quantifying the amount of a MTA1 biomarker present in a biological sample derived from the subject, wherein the subject exhibited a centrifugal (CF) enhancement pattern as measured by dynamic contrast-enhanced magnetic resonance imaging (DCE-MRI); and instructions for quantifying the amount of the MTA1 biomarker in the biological sample and for predicting the subject as having a more aggressive cancer if the MTA1 biomarker is increased in the biological sample derived from the subject as compared to a reference control.

In the kit for determining the aggressiveness of LABC in a subject, the biomarker can be a nucleic acid and the probe can comprise a nucleic acid specific for hybridization to the nucleic acid biomarker. The quantifying the amount of the biomarker can be carried out by one or a combination of Polymerase Chain Reaction, Real Time-Polymerase Chain Reaction, Real Time Reverse Transcriptase-Polymerase Chain Reaction, Northern blot analysis, in situ hybridization, and Array system. The probe can be attached to a solid support.

In the kit for determining the aggressiveness of LABC in a subject, the kit can further comprise reagents for determining the level of the biomarker.

In the kit for determining the aggressiveness of LABC in a subject, the biomarker can be a polypeptide and the probe can comprise an antibody or a binding fragment specific for the polypeptide. The quantifying the amount of biomarker can be carried out by an assay comprising one or a combination of Western Blotting, affinity matrice, and immunoassay.

In the kit for determining the aggressiveness of LABC in a subject, the amount of the biomarker can be a gene expression level.

In the kit for determining the aggressiveness of LABC in a subject, the biological sample can comprise tissues, cells, biopsies, blood, lymph, serum, plasma, urine, saliva, mucus, tears, and combinations thereof. The biological sample can comprise cells.

In the kit for determining the aggressiveness of LABC in a subject, the subject can be a mammal. The subject can be a human.

One aspect of the present disclosure provides a method of determining the aggressiveness of a breast cancer in a subject comprising quantifying the amount of at least one biomarker present in a biological sample derived from the subject, wherein the biomarker is associated with breast cancer aggressiveness. In certain embodiments, the presence of SULTIA1 and/or SULTIA2 are indicative of a less aggressive breast cancer. In other embodiments, the presence of MTA1 is indicative of a more aggressive breast cancer.

Another aspect of the present disclosure provides a method of predicting the likely survival rate of a subject suffering from breast cancer comprising quantifying the amount of at least one biomarker present in a biological sample derived from the subject, wherein the biomarker is associated with patient survival. In certain embodiments, a decreased presence of HYOU1, ARPC5L and/or AVEN are indicative of a greater chance of survival.

Another aspect of the present disclosure provides a method of determining the aggressiveness of a breast cancer in a subject comprising: (a) obtaining a biological sample from a subject; (b) determining the expression level of one or more biomarkers that are associated with breast cancer aggressiveness in the biological sample; (c) comparing the expression level of the biomarkers in the biological sample with that of a control, wherein the presence of one or more of the biomarkers in the sample that is in an amount greater than that of the control indicates the breast cancer is not aggressive; and (d) administering appropriate breast cancer therapy if one or more of the biomarkers are expressed. In certain embodiments, the presence of SULTIA1 and/or SULTIA2 in an amount greater than that of a control are indicative of a less aggressive breast cancer.

Another aspect of the present disclosure provides a method of determining the aggressiveness of a breast cancer of a subject comprising: (a) obtaining a biological sample from a subject; (b) determining the expression level of one or more biomarkers that are associated with breast cancer aggressiveness in the biological sample; (c) comparing the expression level of the biomarkers in the biological sample with that of a control, wherein the presence of one or more of the biomarkers in the sample that is in an amount greater than that of the control indicates the breast cancer is aggressive; and (d) administering an appropriate breast cancer therapy if one or more of the biomarkers are expressed. In other embodiments, the presence of MTA1 in an amount greater than that of a control is indicative of a more aggressive breast cancer.

Yet another aspect of the present disclosure provides a method of predicting the likely survival rate of a subject suffering from breast cancer comprising: (a) obtaining a biological sample from a subject; (b) determining the expression level of one or more biomarkers that are associated with breast cancer survival in the biological sample; (c) comparing the expression level of the biomarkers in the biological sample with that of a control, wherein the presence of one or more of the biomarkers in the sample that is in an amount less than that of the control indicates a greater likelihood of survival; and (d) administering an appropriate breast cancer therapy if one or more of the biomarkers are expressed. In certain embodiments, the presence of HYOU1, ARPC5L and/or AVEN in an amount less than that of a control is indicative of a greater chance of survival.

Another aspect of the present disclosure provides a composition of matter comprising, consisting of, or consisting essentially of: (a) a probe array for determining a biomarker level in a sample, the array comprising of a plurality of probes that hybridizes to one or more biomarkers that are associated with breast cancer aggressiveness and/or likelihood of survival; or (b) a kit for determining a biomarker level in a sample, comprising the probe array of (a) and instructions for carrying out the determination of biomarker expression level in the sample. In certain embodiments the probe array of (a) further comprises a solid support with the plurality of probes attached thereto.

The present disclosure provides a method of determining breast cancer aggressiveness and/or likelihood of survival of a subject suffering from breast cancer on at least one sample obtained from an individual. The individual may be any mammal, but is preferably a human.

The present disclosure may involve obtaining more than one sample, such as two samples, such as three samples, four samples or more from individuals, and preferably the same individual. This allows the relative comparison of expression both as in the presence or absence of at least one protein and/or the level of expression of the at least one protein between the two samples. Alternatively, a single sample may be compared against a "standardized" sample, such a sample comprising material or data from several samples, preferably also from several individuals.

Before analyzing the sample, it will often be desirable to perform one or more sample preparation operations upon the sample. Typically, these sample preparation operations will include such manipulations as concentration, suspension, extraction of intracellular material, e.g., proteins/phosphopeptides from tissue/whole cell samples and the like.

Any method required for the processing of a sample prior to detection by any of the methods noted herein falls within the scope of the present disclosure. These methods are typically well known by a person skilled in the art.

It is within the general scope of the present disclosure to provide methods for the detection of protein biomarker. An aspect of the present disclosure relates to the detection of the proteins as described in the plots and graphs of the figures contained herein. As used herein, the term "detect" or "determine the presence of" refers to the qualitative measurement of undetectable, low, normal, or high concentrations of one or more biomarkers such as, for example, nucleic acids, ribonucleic acids, or polypeptides, proteins, phosphopeptides and other biological molecules. Detection may include 1) detection in the sense of presence versus absence of one or more biomarkers as well as 2) the registration/quantification of the level or degree of expression of one or more biomarkers, depending on the method of detection employed. The term "quantify" or "quantification" may be used interchangeable, and refer to a process of determining the quantity or abundance of a substance in a sample (e.g., a biomarker), whether relative or absolute. For example, quantification may be determined by methods including but not limited to, micro-array analysis, qRT-PCR, band intensity on a Northern or Western blot, or by various other methods known in the art.

The detection of one or more biomarker molecules allows for the determination of breast cancer aggressiveness and/or likelihood of survival. The classification of such conditions is of relevance both medically and scientifically and may provide important information useful for the diagnosis, prognosis and treatment of the condition.

Any method of detection falls within the general scope of the present disclosure. The detection methods may be generic for the detection of proteins, phosphopeptides, nucleic acids, polypeptides and the like. The detection methods may be directed towards the scoring of a presence or absence of one or more biomarker molecules or may be useful in the detection of expression levels.

The detection methods can be divided into two categories herein referred to as in situ methods or screening methods. The term in situ method refers to the detection of protein, phosphopeptide, and/or nucleic acid molecules in a sample wherein the structure of the sample has been preserved. This may thus be a biopsy (e.g., a tissue biopsy) wherein the structure of the tissue is preserved. In situ methods are generally histological i.e. microscopic in nature and include but are not limited to methods such as: in situ hybridization techniques and in situ PCR methods.

Screening methods generally employ techniques of molecular biology and most often require the preparation of the sample material in order to access the nucleic acid and/or polypeptide molecules to be detected. Screening methods include, but are not limited to methods such as: Array systems, affinity matrices, Northern blotting and PCR techniques, such as real-time quantitative RT-PCR.

One aspect of the present disclosure is to provide a probe which can be used for the detection of a protein, phosphopeptide, nucleic acid and/or polypeptide molecule as defined herein. A probe as defined herein is a specific sequence of a nucleic acid and/or polypeptide used to detect nucleic acids and/or polypeptides by hybridization. For example, a nucleic acid is also here any nucleic acid, natural or synthetic such as DNA, RNA, LNA or PNA. A probe may be labeled, tagged or immobilized or otherwise modified according to the requirements of the detection method chosen. A label or a tag is an entity making it possible to identify a compound to which it is associated. It is within the scope of the present disclosure to employ probes that are labeled or tagged by any means known in the art such as but not limited to: radioactive labeling, fluorescent labeling and enzymatic labeling. Furthermore the probe, labeled or not, may be immobilized to facilitate detection according to the detection method of choice and this may be accomplished according to the preferred method of the particular detection method.

Another aspect of the present disclosure regards the detection of nucleic acid and/or polypeptide molecules by any method known in the art. In the following are given examples of various detection methods that can be employed for this purpose, and the present disclosure includes all the mentioned methods, but is not limited to any of these.

In situ hybridization (ISH) applies and extrapolates the technology of nucleic acid and/or polypeptide hybridization to the single cell level, and, in combination with the art of cytochemistry, immunocytochemistry and immunohistochemistry, permits the maintenance of morphology and the identification of cellular markers to be maintained and identified, allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). DNA ISH can be used to determine the structure of chromosomes and the localization of individual genes and optionally their copy numbers. Fluorescent DNA ISH (FISH) can for example be used in medical diagnostics to assess chromosomal integrity. RNA ISH is used to assay expression and gene expression patterns in a tissue/across cells, such as the expression of miRNAs/nucleic acid molecules. Sample cells are treated to increase their permeability to allow the probe to enter the cells, the probe is added to the treated cells, allowed to hybridize at pertinent temperature, and then excess probe is washed away. A complementary probe is labeled with a radioactive, fluorescent or antigenic tag, so that the probe's location and quantity in the tissue can be determined using autoradiography, fluorescence microscopy or immunoassay, respectively. The sample may be any sample as herein described. The probe is likewise a probe according to any probe based upon the biomarkers mentioned herein.

An aspect of the present disclosure includes the method of detection by in situ hybridization as described herein.

In situ PCR is the PCR based amplification of the target nucleic acid sequences prior to ISH. For detection of RNA, an intracellular reverse transcription (RT) step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR the cells are cytocentrifugated onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens. Detection of intracellular PCR-products is achieved by one of two entirely different techniques. In indirect in situ PCR by ISH with PCR-product specific probes, or in direct in situ PCR without ISH through direct detection of labeled nucleotides (e.g. digoxigenin-11-dUTP, fluorescein-dUTP, $^3$H-CTP or biotin-16-dUTP) which have been incorporated into the PCR products during thermal cycling.

An embodiment of the present disclosure concerns the method of in situ PCR as mentioned herein above for the detection of nucleic acid molecules as detailed herein.

A microarray is a microscopic, ordered array of nucleic acids, proteins, small molecules, cells or other substances that enables parallel analysis of complex biochemical samples. A DNA microarray consists of different nucleic acid probes, known as capture probes that are chemically attached to a solid substrate, which can be a microchip, a glass slide or a microsphere-sized bead. Microarrays can be used e.g. to measure the expression levels of large numbers of polypeptides/proteins/nucleic acids simultaneously.

Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays.

An aspect of the present disclosure regards the use of microarrays for the expression profiling of biomarkers in conditions such as breast cancer aggressiveness and/or likelihood of survival. For this purpose, and by way of example, RNA is extracted from a cell or tissue sample, the small RNAs (18-26-nucleotide RNAs) are size-selected from total RNA using denaturing polyacrylamide gel electrophoresis (PAGE). Then oligonucleotide linkers are attached to the 5' and 3' ends of the small RNAs and the resulting ligation products are used as templates for an RT-PCR reaction with 10 cycles of amplification. The sense strand PCR primer has a Cy3 fluorophore attached to its 5' end, thereby fluorescently labelling the sense strand of the PCR product. The PCR product is denatured and then hybridized to the microarray. A PCR product, referred to as the target nucleic acid that is complementary to the corresponding RNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular biomarker, using a number of positive and negative controls and array data normalization methods, which will result in assessment of the level of expression of a particular biomarker.

Several types of microarrays can be employed such as spotted oligonucleotide microarrays, pre-fabricated oligonucleotide microarrays or spotted long oligonucleotide arrays.

In spotted oligonucleotide microarrays the capture probes are oligonucleotides complementary to nucleic acid sequences. This type of array is typically hybridized with amplified.

PCR products of size-selected small RNAs from two samples to be compared that are labelled with two different fluorophores. Alternatively, total RNA containing the small RNA fraction is extracted from the abovementioned two samples and used directly without size-selection of small RNAs, and 3' end labeled using T4 RNA ligase and short RNA linkers labelled with two different fluorophores. The samples can be mixed and hybridized to one single microarray that is then scanned, allowing the visualization of up-regulated and down-regulated biomarker genes in one go. The downside of this is that the absolute levels of gene expression cannot be observed, but the cost of the experiment is reduced by half. Alternatively, a universal reference can be used, comprising of a large set of fluorophore-labelled oligonucleotides, complementary to the array capture probes.

In pre-fabricated oligonucleotide microarrays or single-channel microarrays, the probes are designed to match the sequences of known or predicted biomarkers. There are commercially available designs that cover complete genomes from companies such as Affymetrix, or Agilent. These microarrays give estimations of the absolute value of gene expression and therefore the comparison of two conditions requires the use of two separate microarrays.

Spotted long oligonucleotide arrays are composed of 50 to 70-mer oligonucleotide capture probes, and are produced by either ink-jet or robotic printing. Short Oligonucleotide Arrays are composed of 20-25-mer oligonucleotide probes, and are produced by photolithographic synthesis (Affymetrix) or by robotic printing. More recently, Maskless Array Synthesis from NimbleGen Systems has combined flexibility with large numbers of probes. Arrays can contain up to 390,000 spots, from a custom array design.

An embodiment of the present disclosure concerns the method of microarray use and analysis as described herein.

The terms "PCR reaction", "PCR amplification", "PCR", "pre-PCR", "Q-PCR", "real-time quantitative PCR" and "real-time quantitative RT-PCR" are interchangeable terms used to signify use of a nucleic acid amplification system, which multiplies the target nucleic acids being detected. Examples of such systems include the polymerase chain reaction (PCR) system and the ligase chain reaction (LCR) system. Other methods recently described and known to the person of skill in the art are the nucleic acid sequence based amplification and Q Beta Replicase systems. The products formed by said amplification reaction may or may not be monitored in real time or only after the reaction as an end-point measurement.

Real-time quantitative RT-PCR is a modification of polymerase chain reaction used to rapidly measure the quantity of a product of polymerase chain reaction. It is preferably done in real-time, thus it is an indirect method for quantitatively measuring starting amounts of DNA, complementary DNA or ribonucleic acid (RNA). This is commonly used for the purpose of determining whether a genetic sequence is present or not, and if it is present the number of copies in the sample. There are 3 methods which vary in difficulty and detail. Like other forms of polymerase chain reaction, the process is used to amplify DNA samples, using thermal cycling and a thermostable DNA polymerase.

The three commonly used methods of quantitative polymerase chain reaction are through agarose gel electrophoresis, the use of SYBR Green, a double stranded DNA dye, and the fluorescent reporter probe. The latter two of these three can be analysed in real-time, constituting real-time polymerase chain reaction method.

Agarose gel electrophoresis is the simplest method, but also often slow and less accurate then other methods, depending on the running of an agarose gel via electrophoresis. It cannot give results in real time. The unknown sample and a known sample are prepared with a known concentration of a similarly sized section of target DNA for amplification. Both reactions are run for the same length of time in identical conditions (preferably using the same primers, or at least primers of similar annealing temperatures). Agarose gel electrophoresis is used to separate the products of the reaction from their original DNA and spare primers. The relative quantities of the known and unknown samples are measured to determine the quantity of the unknown. This method is generally used as a simple measure of whether the probe target sequences are present or not, and rarely as 'true' Q-PCR.

Using SYBR Green dye is more accurate than the gel method, and gives results in real time. A DNA binding dye binds all newly synthesized double stranded (ds)DNA and an increase in fluorescence intensity is measured, thus allowing initial concentrations to be determined. However, SYBR Green will label all dsDNA including any unexpected PCR products as well as primer dimers, leading to potential complications and artefacts. The reaction is prepared as usual, with the addition of fluorescent dsDNA dye. The reaction is run, and the levels of fluorescence are monitored; the dye only fluoresces when bound to the dsDNA. With reference to a standard sample or a standard curve, the dsDNA concentration in the PCR can be determined.

The fluorescent reporter probe method is the most accurate and most reliable of the methods. It uses a sequence-specific nucleic acid based probe so as to only quantify the probe sequence and not all double stranded DNA. It is commonly carried out with DNA based probes with a fluorescent reporter and a quencher held in adjacent positions, so-called dual-labelled probes. The close proximity of the reporter to the quencher prevents its fluorescence; it is only on the breakdown of the probe that the fluorescence is detected. This process depends on the 5' to 3' exonuclease activity of the polymerase involved. The real-time quantitative PCR reaction is prepared with the addition of the dual-labelled probe. On denaturation of the double-stranded DNA template, the probe is able to bind to its complementary sequence in the region of interest of the template DNA (as the primers will too). When the PCR reaction mixture is heated to activate the polymerase, the polymerase starts synthesizing the complementary strand to the primed single stranded template DNA. As the polymerisation continues it reaches the probe bound to its complementary sequence, which is then hydrolysed due to the 5'-3' exonuclease activity of the polymerase thereby separating the fluorescent reporter and the quencher molecules. This results in an increase in fluorescence, which is detected. During thermal cycling of the real-time PCR reaction, the increase in fluorescence, as released from the hydrolysed dual-labelled probe in each PCR cycle is monitored, which allows accurate determination of the final, and so initial, quantities of DNA.

Any method of PCR that can determine the expression of a nucleic acid molecule as defined herein falls within the scope of the present disclosure. A preferred embodiment of the present disclosure includes the real-time quantitative RT-PCR method, based on the use of either SYBR Green dye or a dual-labelled probe for the detection and quantification of nucleic acids according to the herein described.

An aspect of the present disclosure includes the detection of the nucleic acid molecules herein disclosed by techniques such as Northern blot analysis. Many variations of the protocol exist.

The following examples are offered by way of illustration and not by way of limitation.

EXAMPLES

Example 1

Identification of Biomarkers for Locally Advanced (LABC) and Inflammatory Breast Cancer (IBC)

Between 2000 and 2004, 47 LABC patients were enrolled in an IRB-approved phase I/II clinical trial at Duke University Medical Center (Durham, N.C.). RNA from pre-treatment Ultrasound guided core biopsies were assayed by gene expression analysis. In 20 of these patients, pretreatment dynamic contrast-enhanced magnetic resonance imaging (DCE-MRI) features were analyzed for association with treatment response in LABC including its subset of IBC patients.[5,6] The subgroup of 20 patients were chosen from the whole group of 47, because their DCE-MRI data was attained using the same protocol, and because these patients all received the same dosage of neoadjuvant chemotherapy and hyperthermia.[5]. Importantly, two distinct patterns of image enhancement were observed in the image analysis: i) centripetal (CP) which was an inhomogeneous ring-type enhancement; and ii) centrifugal (CF), which was characterized by more homogenous enhancement from center to periphery.[5,7,8]

It was hypothesized that gene expression differences would exist between tumors that exhibit CP vs. CF perfusion patterns. The potential linkage between gene expression profiles and DCE-MRI parameters was analyzed as described herein below in LABC patients. In addition, the association was analyzed between the long-term overall survival (OS) of the patients and gene expression profiles in the IBC subgroup. Regardless of the availability of imaging data, the association was analyzed between the candidate genes described herein and OS using the publically available "The Cancer Genome Atlas" (TCGA) database.

Methods

Study Population

The selection of the study population has been described in detail elsewhere.[4,6] Briefly, between 2000 and 2004, 47 LABC patients were enrolled for an IRB-approved phase I/II clinical trial at Duke University Medical Center (Durham, N.C.). Patients were treated with neoadjuvant liposomal doxorubicin and paclitaxel in combination with local breast hyperthermia, every three weeks for four cycles. Three patients did not complete therapy. From the total of 47 patients enrolled in the clinical trial, pretreatment biopsies, collected under ultrasound guidance, were available from 37 patients, including 13 with a diagnosis of IBC. All 37 pretreatment biopsies were confirmed to have at least 60% invasive disease throughout the core sample before RNA harvesting. RNA was prepared, probe generated, and used for hybridization to Affymetrix U133 Plus 2.0 GeneChip arrays.[4,6]

DCE-MRI

The image analysis protocol has previously been described in detail for characterization of the CP and CF perfusion patterns.[5] Briefly, the DCE-MRI was performed over 30 minutes following bolus injection of gadopentetate-based contrast agent. Two distinct patterns of enhancement of CP and CF were observed (data not shown). In addition, the slope of the wash-in parameter (WiP) and the wash-out parameter (WoP) were calculated. The WiP is an indication of tumor permeability and vascularity. The WoP reflects the rate of return of the contrast agent to the blood. WoP values have been reported to be influenced by at least 3 factors: tumor size, tumor vascularity, and volume of extra cellular space.[5,8] The CP/CF perfusion patterns and the WiP/WoP values were combined to derive a novel morphophysiologic score (MPTS), and it was reported that the patient's pathological response and the MPTS were highly correlated.[5]

Data Analysis & Statistical Considerations:

The genomic data discussed in the study described herein below has been deposited in the NCBI's Gene Expression Omnibus.[9] The deposited data are accessible though the GEO Series accession number GSE52322; "Novel linkages between DCE-MRI and genomic profiling in locally advanced and inflammatory breast cancer".

From the total of 20 patients who had the DCE-MRI, 15 patients had both the imaging and genomic data available. For the study described herein below, LABC samples were assayed using the Affymetrix U133 Plus 2.0 GeneChip arrays which interrogates mRNA expression, based on 54,675 probe sets. All statistical analyses were conducted using the R statistical environment.[10,11] The chips were pre-processed using the RMA algorithm.[12] Ordination methods (e.g., multi-dimensional scaling) were then used to identify experimental artifacts, such as batch effects.[13] Pre-processing was conducted on the basis of all available samples from the LABC study deemed to be of good quality regardless of the availability of the phenotype.

For studying the association between the gene expression profile and the CP versus CF morphology, Wilcoxon rank sum test was used to prioritize the features (probe sets) according to statistical significance. Association between feature expression level and survival was assessed using a Cox rank score test.[14] As the feature selection process was considered to be hypothesis generating, the P-values reported have not been adjusted for multiple testing. The associations between expression level and OS for the implicated genes were further assessed in a published cohort from the "The Cancer Genome Atlas" (TCGA) for their breast cancer dataset using the Breast Invasive Carcinoma project (N=825 cases).[15] The TCGA mRNA data were retrieved from the Cancer Genomic Data Server (CGDS) through the Computational Biology Center Portal (cBio). The cdgsr extension package was used to execute the retrieval.

Results

Of the fifteen patients with both genomic and imaging information, ten had the CP enhancement pattern while five had the CF pattern. Following mRNA expression analysis, genes were identified that were differentially expressed in the CP vs CF pattern. Table I shows the 152 annotated probes that were differentially expressed in CF vs. CP enhancement patterns. A negative test statistic represents higher expression level of the particular gene in the CF pattern, and a positive test statistic represents higher expression level of the particular gene in the CP pattern. Approximately 80% of the probes had higher expression levels in the CP pattern while only 20% had higher expression levels in the CF pattern.

TABLE I

Differentially expressed genes in the CF vs. CP enhancement pattern.

| Probe ID | Test Statistics | SYMBOL |
|---|---|---|
| 202247_s_at | −6.31 | MTA1 |
| 219833_s_at | 6.31 | EFHC1 |
| 1556507_at | −6.30 | LOC100507274 |
| 203615_x_at | 6.30 | SULT1A1 |
| 206600_s_at | 6.30 | SLC16A5 |
| 207122_x_at | 6.30 | SULT1A2 |

TABLE I-continued

Differentially expressed genes in the CF vs. CP enhancement pattern.

| Probe ID | Test Statistics | SYMBOL |
|---|---|---|
| 209859_at | 6.30 | TRIM9 |
| 211385_x_at | 6.30 | SULT1A2 |
| 212207_at | 6.30 | MED13L |
| 219639_x_at | 6.30 | PARP6 |
| 219765_at | 6.30 | ZNF329 |
| 219985_at | −6.30 | HS3ST3A1 |
| 230435_at | 6.30 | FAM228B |
| 231838_at | 6.30 | PABPC1L |
| 235729_at | 6.30 | ZNF514 |
| 236115_at | 6.30 | HTR7P1 |
| 242079_at | 6.30 | RGS12 |
| 230623_x_at | −5.42 | USP28 |
| 202328_s_at | 5.42 | PKD1 |
| 203830_at | 5.42 | C17orf75 |
| 214218_s_at | 5.42 | XIST |
| 221728_x_at | 5.42 | XIST |
| 222925_at | 5.42 | DCDC2 |
| 226344_at | 5.42 | ZMAT1 |
| 227074_at | 5.42 | LOC100131564 |
| 231437_at | 5.42 | SLC35D2 |
| 232683_s_at | 5.42 | PARP6 |
| 233929_x_at | 5.42 | WASH3P |
| 238987_at | 5.42 | B4GALT1 |
| 228730_s_at | 5.42 | SCRN2 |
| 238862_at | 4.87 | MFSD4 |
| 205625_s_at | 4.86 | CALB1 |
| 212925_at | 4.86 | C19orf21 |
| 218164_at | 4.86 | SPATA20 |
| 221919_at | 4.86 | HNRNPA1 |
| 223295_s_at | 4.86 | LUC7L |
| 32259_at | 4.86 | EZH1 |
| 37547_at | 4.86 | BBS9 |
| 202792_s_at | 4.86 | PPP6R2 |
| 225071_at | −4.86 | NUS1 |
| 1565339_at | 4.71 | DNAH10 |
| 223546_x_at | 4.69 | LUC7L |
| 228861_at | 4.69 | CDS2 |
| 205316_at | −4.69 | SLC15A2 |
| 203938_s_at | 4.68 | TAF1C |
| 212049_at | 4.68 | WIPF2 |
| 212776_s_at | 4.68 | OBSL1 |
| 220168_at | 4.68 | CASC1 |
| 222665_at | 4.68 | RMDN1 |
| 226562_at | 4.68 | ZSCAN29 |
| 227775_at | 4.68 | CELF6 |
| 228264_at | 4.68 | ACCS |
| 234710_s_at | 4.68 | PARP6 |
| 235938_at | 4.68 | ARMC9 |
| 242305_at | 4.68 | LOC645513 |
| 37860_at | 4.68 | ZNF337 |
| 37953_s_at | 4.68 | ASIC1 |
| 231513_at | −4.68 | KCNJ2 |
| 1552960_at | −4.48 | LRRC15 |
| 219551_at | −4.48 | EAF2 |
| 222501_s_at | −4.48 | REPIN1 |
| 223991_s_at | −4.48 | GALNT2 |
| 1556381_at | 4.48 | NAA15 |
| 201167_x_at | −4.48 | ARHGDIA |
| 203126_at | −4.48 | IMPA2 |
| 213459_at | 4.48 | RPL37A |
| 217517_x_at | −4.48 | SRPK2 |
| 235937_at | 4.48 | OCLN |
| 203409_at | 4.48 | DDB2 |
| 203569_s_at | 4.48 | OFD1 |
| 205527_s_at | 4.48 | GEMIN4 |
| 208006_at | 4.48 | FOXI1 |
| 218385_at | 4.48 | MRPS18A |
| 241833_at | 4.48 | PEX5L |
| 212744_at | 4.26 | BBS4 |
| 1556715_at | 4.26 | PRPSAP1 |
| 1557073_s_at | 4.26 | TTBK2 |
| 203804_s_at | 4.26 | LUC7L3 |
| 206967_at | 4.26 | CCNT1 |
| 220390_at | 4.26 | AGBL2 |
| 221499_s_at | 4.26 | STX16 |
| 238818_at | 4.26 | KIAA1429 |
| 214606_at | −4.24 | TSPAN2 |
| 47553_at | 4.23 | DFNB31 |
| 1568822_at | 4.23 | GTPBP5 |
| 204217_s_at | 4.23 | RTN2 |
| 206515_at | 4.23 | CYP4F3 |
| 213264_at | 4.23 | PCBP2 |
| 221812_at | 4.23 | FBXO42 |
| 219667_s_at | −4.23 | BANK1 |
| 216896_at | −4.08 | COL4A3 |
| 238551_at | −4.08 | FUT11 |
| 1554447_at | 4.08 | JPX |
| 1555677_s_at | −4.08 | SMC1A |
| 1557014_a_at | 4.08 | FAM201A |
| 1557394_at | 4.08 | DLGAP4 |
| 202392_s_at | 4.08 | PISD |
| 212021_s_at | −4.08 | MKI67 |
| 218686_at | 4.08 | RHBDF1 |
| 221984_s_at | 4.08 | FAM134A |
| 224044_at | 4.08 | RHOT1 |
| 226198_at | 4.08 | TOM1L2 |
| 228787_at | 4.08 | BCAS4 |
| 229666_s_at | −4.08 | CSTF3 |
| 233945_at | 4.08 | UGGT2 |
| 236313_at | −4.08 | CDKN2B |
| 239247_at | 4.08 | CD99P1 |
| 239753_at | 4.08 | ZNF252P |
| 1559607_s_at | −4.07 | GBP6 |
| 1568836_at | −4.07 | CLK4 |
| 242331_x_at | −4.07 | LOC642236 |
| 218810_at | 4.07 | ZC3H12A |
| 203848_at | 4.07 | AKAP8 |
| 204231_s_at | 4.07 | FAAH |
| 212775_at | 4.07 | OBSL1 |
| 217501_at | 4.07 | CIAO1 |
| 220041_at | 4.07 | PIGZ |
| 224522_s_at | 4.07 | DCAKD |
| 224882_at | 4.07 | ACSS1 |
| 226186_at | 4.07 | TMOD2 |
| 219184_x_at | 3.99 | TIMM22 |
| 1553978_at | 3.96 | MEF2BNB |
| 1554448_at | 3.96 | JPX |
| 1557966_x_at | 3.96 | MTERFD2 |
| 1559449_a_at | 3.96 | LOC100996381 |
| 212081_x_at | 3.96 | PRRC2A |
| 222819_at | 3.96 | CTPS2 |
| 226269_at | 3.96 | GDAP1 |
| 227402_s_at | 3.96 | UTP23 |
| 244084_at | 3.96 | AIFM3 |
| 1557226_a_at | −3.96 | ASPG |
| 1563369_at | 3.96 | LINC00173 |
| 209347_s_at | −3.96 | MAF |
| 224588_at | 3.96 | XIST |
| 1558497_a_at | −3.85 | LOC100505609 |
| 1560115_a_at | −3.85 | KIAA1217 |
| 226668_at | 3.85 | WDSUB1 |
| 1552765_x_at | 3.85 | TMEM67 |
| 1560089_at | 3.85 | LOC100289019 |
| 203609_s_at | 3.85 | ALDH5A1 |
| 212444_at | 3.85 | GPRC5A |
| 218410_s_at | 3.85 | PGP |
| 218740_s_at | 3.85 | CDK5RAP3 |
| 221879_at | 3.85 | CALML4 |
| 225758_s_at | 3.85 | TUBGCP6 |
| 226168_at | 3.85 | ZFAND2B |
| 226689_at | 3.85 | CISD2 |
| 227669_at | 3.85 | MPC2 |
| 230511_at | 3.85 | CREM |
| 232566_at | −3.85 | NOL6 |
| 235405_at | 3.85 | GSTA4 |
| 236104_at | 3.85 | HNRPLL |

Figure 1B:
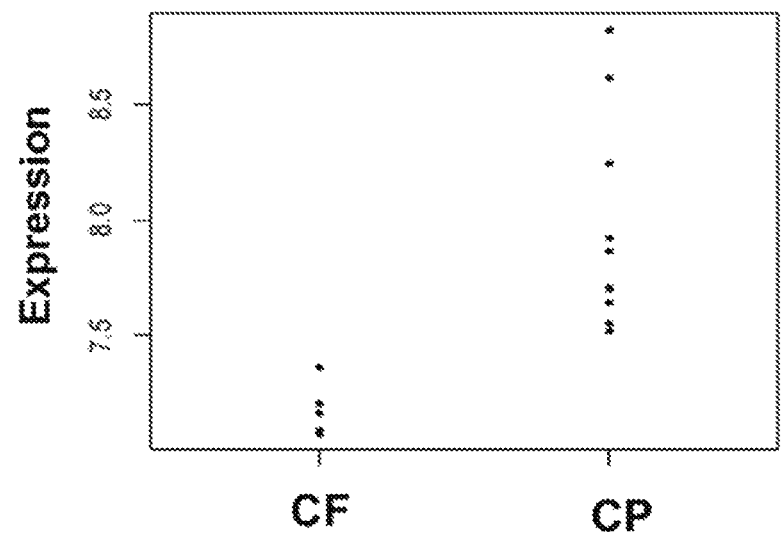

As seen in Table I, CP pattern was found to have higher expression of genes involved in a component of sulfur metabolism pathway. In particular, the genes were two members of the sulfotransferase family: i) sulfotransferase family, cytosolic, 1A, phenol-preferring, member 1 (SULT1A1), and ii) sulfotransferase family, cytosolic, 1A, phenol-preferring, member 2 (SULT1A2). FIGS. 1A and 1B, respectively, show SULT1A1 and SULT1A2 expression levels in the CF enhancement pattern compared to the CP. This analysis demonstrates an over expression of SULTs (SULT1A1 and SULT1A2) in the CP enhancement compared to CF.

Figure 2A:
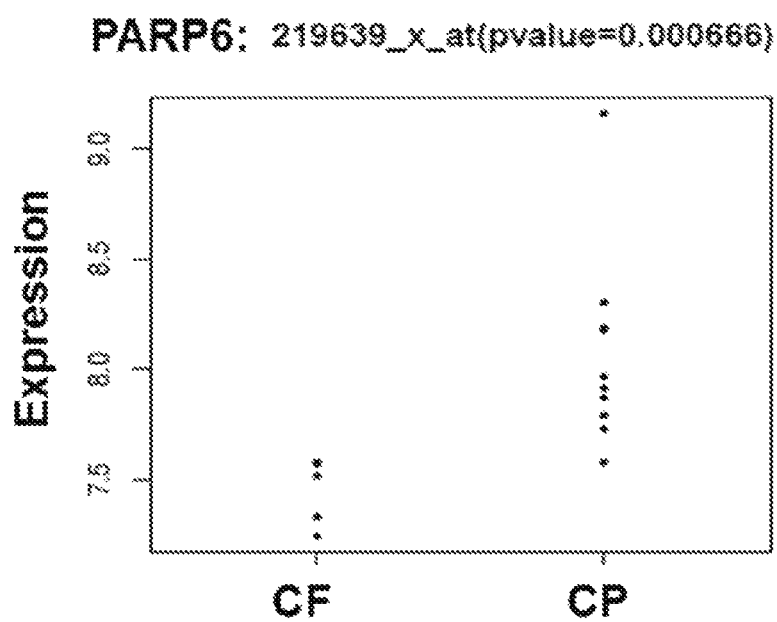
FIGS. 2A & 2B are graphs showing differential gene expression of PARP6 (A) and MTA1 (B) in CP and CF LABC samples according to one or more embodiments of the present disclosure.

In addition, similarly higher RNA expression levels of poly(ADP-ribose) polymerase, member 6 (PARP6) were observed for CP. FIG. 2A shows PARP6 exhibited higher expression levels in the CP enhancement patterns as compared to the CP patterns.

Figure 2B:
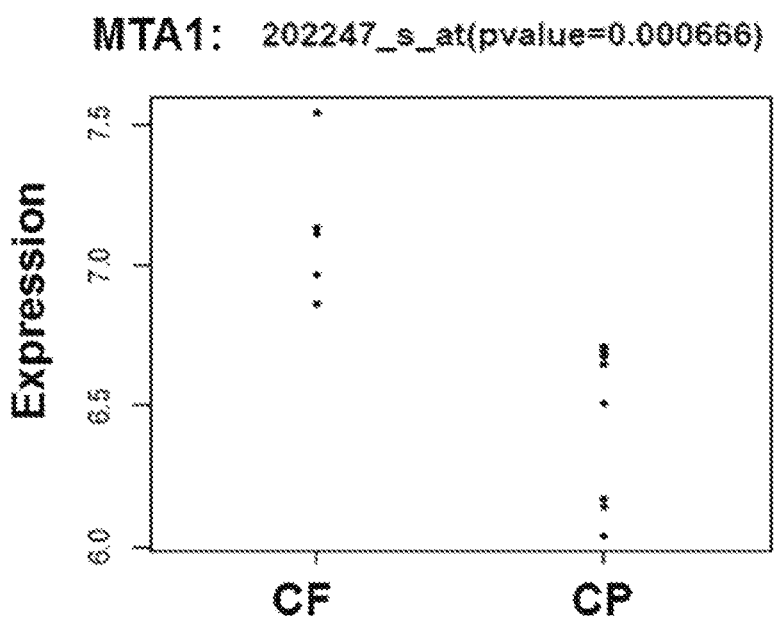

The metastasis tumor antigen1(MTA1) was also differentially expressed in the CP vs. CF morphology. FIG. 2B shows differential expression levels of MTA1 in the CF enhancement pattern compared to the CP enhancement pattern. However, in contrast to the previous three genes, MTA1 was overexpressed in CF. Due to this finding that i) CF has a higher expression of MTA1 (p-value=0.0006), and ii) MTA1's function as ESR1 co-repressor, the data were analyzed for ESR1 expression levels in CP vs. CF. The results of this analysis showed lower ESR1 expression in the CF phenotype as compared to CP in one of the probes linked to ESR1 (ESR1:205225_at p-value=0.028) (data not shown).

The follow up time for the patients in this trial was 10 years and the median follow-up time was 8.4 years. This long follow up time provided a good opportunity to analyze the gene expression data for its association with overall survival (OS). The association was analyzed between the genomic expression data in the subgroup of the 13 IBC cases and overall survival. The sample analysis was limited to the IBC cases because these cases provided the largest subgroup out of the total 47 cases with a more uniform tumor type. The results are shown in Table II below. The Hazard Ratio (HR) >1.0 in Table II indicates that over expression of these genes was associated with shortened survival in IBC patients.

TABLE II

Gene expression profiles associated with overall survival (OS) in IBC patients.

| Probe | Symbol | GenBank | HR |
|---|---|---|---|
| 226372_at | CHST11 | AI123348 | 2.4 |
| 226342_at | SPTBN1 | AW593244 | 2.1 |
| 200825_s_at | HYOU1 | NM_006389 | 1.7 |
| 236361_at | GALNTL2 | BF432376 | 1.8 |
| 1553438_at | C11orf72 | NM_173578 | 1.7 |
| 207266_x_at | RBMS1 | NM_016837 | 1.8 |
| 1553222_at | OXER1 | AB083055 | 1.6 |
| 210785_s_at | C1orf38 | AB035482 | 1.6 |
| 1553971_a_at | GATS | AL831967 | 1.6 |
| 226914_at | ARPC5L | AU158936 | 1.8 |
| 213274_s_at | CTSB | AA020826 | 1.6 |
| 212701_at | TLN2 | AB002318 | 1.6 |
| 213680_at | KRT6B | AI831452 | 1.6 |
| 32094_at | CHST3 | AB017915 | 1.5 |
| 202720_at | TES | NM_015641 | 1.8 |
| 209325_s_at | RGS16 | U94829 | 1.6 |
| 224767_at | RPL37 | AL044126 | 1.5 |
| 213093_at | PRKCA | AI471375 | 1.6 |
| 223309_x_at | PNPLA8 | BG025248 | 1.6 |
| 201387_s_at | UCHL1 | NM_004181 | 1.6 |

TABLE II-continued

Gene expression profiles associated with overall survival (OS) in IBC patients.

| Probe | Symbol | GenBank | HR |
|---|---|---|---|
| 229779_at | COL4A4 | BF476080 | 1.6 |
| 221766_s_at | FAM46A | AW246673 | 1.5 |
| 203865_s_at | ADARB1 | NM_015833 | 1.6 |
| 229549_at | CALU | AA868461 | 1.6 |
| 223340_at | ATL1 | AF131801 | 1.5 |
| 215157_x_at | PABPC1 | A1734929 | 1.5 |
| 213146_at | KDM6B | AA521267 | 1.8 |
| 228489_at | TM4SF18 | AI721164 | 1.6 |
| 201645_at | TNC | NM_002160 | 1.7 |
| 230656_s_at | CIRH1A | AL578336 | 1.5 |
| 231223_at | CSMD1 | R41565 | 1.5 |
| 208249_s_at | TGDS | NM_014305 | 1.6 |
| 226814_at | ADAMTS9 | AI431730 | 1.6 |
| 201422_at | IFI30 | NM_006332 | 1.5 |
| 225582_at | ITPRIP | AA425726 | 1.6 |
| 219366_at | AVEN | NM_020371 | 1.5 |
| 204469_at | PTPRZ1 | NM_002851 | 1.5 |
| 203836_s_at | MAP3K5 | D84476 | 1.6 |
| 221641_s_at | ACOT9 | AF241787 | 1.5 |
| 230744_at | FSTL1 | N22766 | 1.7 |
| 226448_at | FAM89A | AI130705 | 1.5 |
| 202897_at | SIRPA | AB023430 | 1.6 |
| 1555841_at | C9orf30 | BQ014020 | 1.5 |
| 236331_at | CDKL2 | AW299729 | 1.5 |

Three of the genes found to be associated with OS in the IBC patients and shown in Table II are: i) hypoxia up-regulated protein 1 (HYOU1, 200825_s_at, P-value=0.0002), ii) actin related protein 2/3 complex, subunit 5-like (ARPC5L, 226914_at, P-value=0.0004), and iii) apoptosis caspase activation inhibitor (AVEN, 219366_at, P-value=0.001). The effects of HYOU1 and ARPC5L gene expression patterns on overall survival in IBC patients are shown in FIGS. 3A and 3B, respectively. These long term follow up data demonstrate that lower expression levels of HYOU1 and ARPC5L are associated with better overall survival outcomes in IBC ("Survival Time" unit in FIGS. 3A & 3B is in years; three of the patients who were still alive at the time of the data analysis are represented with a "triangle" symbol in the graphs). In particular, low expression of HYOU1, ARPC5, and AVEN were all associated with better long term overall survival (the data for AVEN is not shown).

Figure 4A:
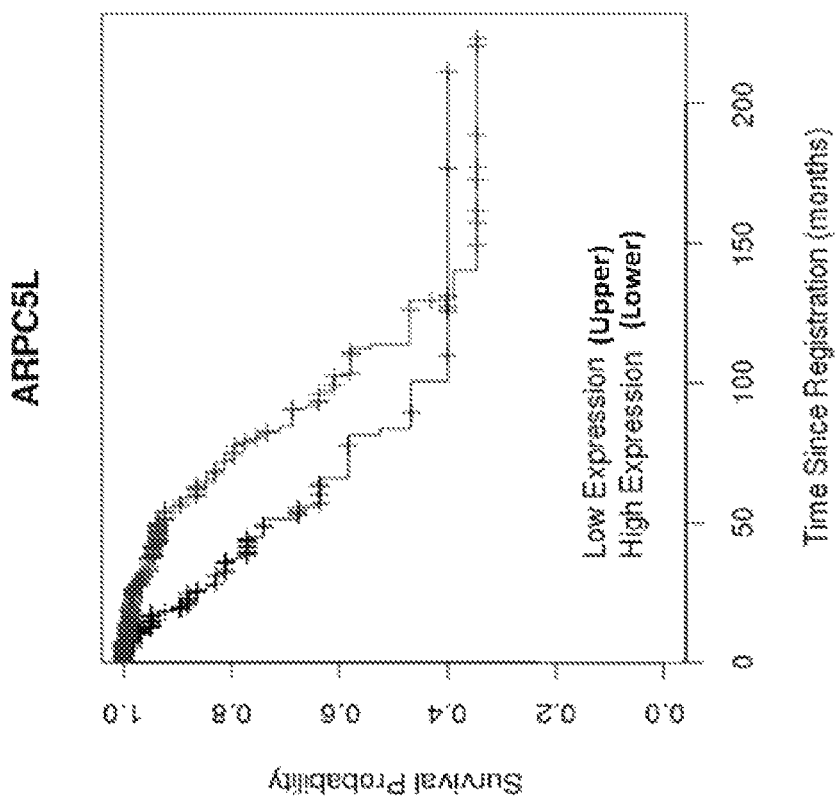
FIGS. 4A & 4B are graphs showing survival probability versus time since registration for LABC patients based on low versus high gene expression of MTA1 (A) and ARPC5L (B) using a publically available TCGA database for external confirmation according to one or more embodiments of the present disclosure.
Figure 4B:
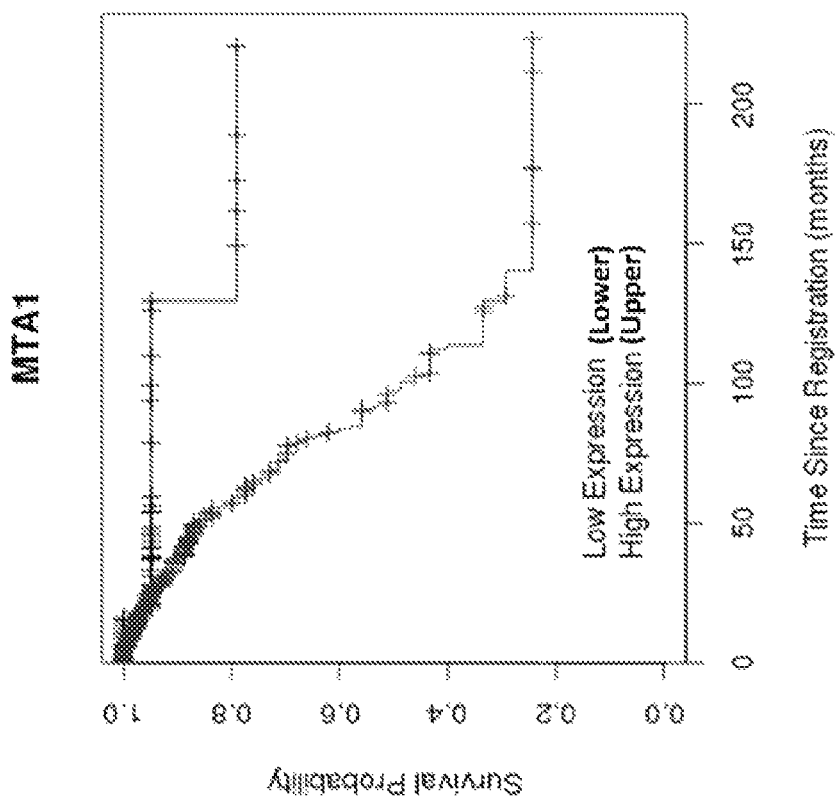

In addition to the foregoing experiments, the publically available TCGA data base was used for external confirmation of the results. Since the TCGA does not include the imaging data used for CP vs. CF classification, the association was looked at between the expression level of the genes described herein above and OS. In the TCGA cohort, differential expression of two of the genes exhibited significant association with overall survival of LABC patients: 1) ARPC5L (TCGA p-value=0.039) and 2) MTA1 (TCGA p-value=0.003). These external confirmation data using the TCGA cohort are shown in FIGS. 4A & 4B for MTA1 and ARPC5L, respectively. Out of the genes analyzed, MTA1 and ARPC5L showed significant association with overall survival in the TCGA breast cancer database as well.

The results provided herein indicate that the two DCE-MRI enhancement patterns of CF and CP have distinct gene expression profiles. Out of the top 200 probe sets that were differentially expressed in CF vs. CP (p-value <0.008), 82% of the probes had higher expression levels in the CP enhancement pattern and only 18% had higher expression levels in CF.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

REFERENCES

1. Cristofanilli M, Buchholz T A (2010) Proceedings of the First International Inflammatory Breast Cancer Conference. Cancer 116: 2729.
2. Dawood S, Merajver S D, Viens P, Vermeulen P B, Swain S M, et al. (2011) International expert panel on inflammatory breast cancer: consensus statement for standardized diagnosis and treatment. Ann Oncol 22: 515-523.
3. Robertson F M, Bondy M, Yang W, Yamauchi H, Wiggins S, et al. (2010) Inflammatory breast cancer: the disease, the biology, the treatment. C A Cancer J Clin 60: 351-375.
4. Vujaskovic Z, Kim D W, Jones E, Lan L, McCall L, et al. (2010) A phase I/II study of neoadjuvant liposomal doxorubicin, paclitaxel, and hyperthermia in locally advanced breast cancer. Int J Hyperthermia 26: 514-521.
5. Craciunescu 01, Blackwell K L, Jones E L, Macfall J R, Yu D, et al. (2009) DCE-MRI parameters have potential to predict response of locally advanced breast cancer patients to neoadjuvant chemotherapy and hyperthermia: a pilot study. Int J Hyperthermia 25: 405-415.
6. Dressman H K, Hans C, Bild A, Olson J A, Rosen E, et al. (2006) Gene expression profiles of multiple breast cancer phenotypes and response to neoadjuvant chemotherapy. Clin Cancer Res 12: 819-826.
7. Daniel B L, Yen Y F, Glover G H, Ikeda D M, Birdwell R L, et al. (1998) Breast disease: dynamic spiral M R imaging. Radiology 209: 499-509.
8. Helbich T H (2000) Contrast-enhanced magnetic resonance imaging of the breast. Eur J Radiol 34: 208-219.
9. Barrett T, Wilhite S E, Ledoux P, Evangelista C, Kim I F, et al. (2013) NCBI GEO: archive for functional genomics data sets—update. Nucleic Acids Research 41: D991-D995.
10. Gentleman R (2005) Bioinformatics and computational biology solutions using R and Bioconductor. New York: Springer Science+Business Media. xix, 473 p. p.
11. Gentleman R C, Carey V J, Bates D M, Bolstad B, Dettling M, et al. (2004) Bioconductor: open software development for computational biology and bioinformatics. Genome Biol 5: R80.
12. Irizarry R A, Bolstad B M, Collin F, Cope L M, Hobbs B, et al. (2003) Summaries of Affymetrix GeneChip probe level data. Nucleic Acids Res 31: e15.
13. K. V. Mardia J T K, and J. M. Bibby. (1979) Multivariate Analysis. Academic Press.
14. Schoenfeld D (1982) Partial Residuals for The Proportional Hazards Regression Model. Biometrika 69: 239-241.
15. (2012) Ovarian cancer and body size: individual participant meta-analysis including 25,157 women with ovarian cancer from 47 epidemiological studies. PLoS Med 9: e1001200.
16. Viglianti B L, Lora-Michiels M, Poulson J M, Lan L, Yu D, et al. (2009) Dynamic contrast-enhanced magnetic resonance imaging as a predictor of clinical outcome in canine spontaneous soft tissue sarcomas treated with thermoradiotherapy. Clin Cancer Res 15: 4993-5001.
17. Aust S, Obrist P, Klimpfinger M, Tucek G, Jager W, et al. (2005) Altered expression of the hormone- and xenobiotic-metabolizing sulfotransferase enzymes 1A2 and 1C1 in malignant breast tissue. Int J Oncol 26: 1079-1085.
18. Wang Y, Spitz M R, Tsou A M, Zhang K, Makan N, et al. (2002) Sulfotransferase (SULT) 1A1 polymorphism as a predisposition factor for lung cancer: a case-control analysis. Lung Cancer 35: 137-142.
19. Falany J L, Falany C N (2007) Interactions of the human cytosolic sulfotransferases and steroid sulfatase in the metabolism of tibolone and raloxifene. J Steroid Biochem Mol Biol 107: 202-210.
20. Kim M Y, Zhang T, Kraus W L (2005) Poly(ADP-ribosyl)ation by PARP-1: 'PAR-laying' NAD+into a nuclear signal. Genes Dev 19: 1951-1967.
21. Ame J C, Spenlehauer C, de Murcia G (2004) The PARP superfamily. Bioessays 26: 882-893.
22. Ossovskaya V, Koo I C, Kaldlian E P, Alvares C, Sherman B M (2010) Upregulation of Poly (ADP-Ribose) Polymerase-1 (PARP1) in Triple-Negative Breast Cancer and Other Primary Human Tumor Types. Genes Cancer 1: 812-821.
23. Rajesh M, Mukhopadhyay P, Batkai S, Godlewski G, Hasko G, et al. (2006) Pharmacological inhibition of poly(ADP-ribose) polymerase inhibits angiogenesis. Biochem Biophys Res Commun 350: 352-357.
24. Pyriochou A, Olah G, Deitch E A, Szabo C, Papapetropoulos A (2008) Inhibition of angiogenesis by the poly (ADP-ribose) polymerase inhibitor PJ-34. Int J Mol Med 22: 113-118.
25. Tutt A, Robson M, Garber J E, Domchek S M, Audeh M W, et al. Oral poly(ADP-ribose) polymerase inhibitor olaparib in patients with BRCA1 or BRCA2 mutations and advanced breast cancer: a proof-of-concept trial. The Lancet 376: 235-244.
26. Dent R A, Lindeman G J, Clemons M, Wildiers H, Chan A, et al. (2013) Phase I trial of the oral PARP inhibitor olaparib in combination with paclitaxel for first- or second-line treatment of patients with metastatic triple-negative breast cancer. Breast Cancer Res 15: R88.
27. Al-Ejeh F, Shi W, Miranda M, Simpson P T, Vargas A C, et al. (2013) Treatment of triple-negative breast cancer using anti-EGFR-directed radioimmunotherapy combined with radiosensitizing chemotherapy and PARP inhibitor. J Nucl Med 54: 913-921.
28. Bundred N, Gardovskis J, Jaskiewicz J, Eglitis J, Paramonov V, et al. (2013) Evaluation of the pharmacodynamics and pharmacokinetics of the PARP inhibitor olaparib: a phase I multicentre trial in patients scheduled for elective breast cancer surgery. Invest New Drugs 31: 949-958.
29. Toh Y, Kuwano H, Mori M, Nicolson G L, Sugimachi K (1999) Overexpression of metastasis-associated MTA1 mRNA in invasive oesophageal carcinomas. Br J Cancer 79: 1723-1726.

30. Giannini R, Cavallini A (2005) Expression analysis of a subset of coregulators and three nuclear receptors in human colorectal carcinoma. Anticancer Res 25: 4287-4292.
31. Kidd M, Modlin I M, Mane S M, Camp R L, Eick G, et al. (2006) The role of genetic markers—NAP1L1, MAGE-D2, and MTA1—in defining small-intestinal carcinoid neoplasia. Ann Surg Oncol 13: 253-262.
32. Dannenmann C, Shabani N, Friese K, Jeschke U, Mylonas I, et al. (2008) The metastasis-associated gene MTA1 is upregulated in advanced ovarian cancer, represses ERbeta, and enhances expression of oncogenic cytokine GRO. Cancer Biol Ther 7: 1460-1467.
33. Hofer M D, Tapia C, Browne T J, Mirlacher M, Sauter G, et al. (2006) Comprehensive analysis of the expression of the metastasis-associated gene 1 in human neoplastic tissue. Arch Pathol Lab Med 130: 989-996.
34. Jang K-S, Paik S S, Chung H, Oh Y-H, Kong G (2006) MTA1 overexpression correlates significantly with tumor grade and angiogenesis in human breast cancers. Cancer Science 97: 374-379.
35. Martin M D, Hilsenbeck S G, Mohsin S K, Hopp T A, Clark G M, et al. (2006) Breast tumors that overexpress nuclear metastasis-associated 1 (MTA1) protein have high recurrence risks but enhanced responses to systemic therapies. Breast Cancer Res Treat 95: 7-12.
36. Toh Y, Nicolson G (2009) The role of the <i>MTA</i> family and their encoded proteins in human cancers: molecular functions and clinical implications. Clinical and Experimental Metastasis 26: 215-227.
37. Kumar R, Wang R A, Mazumdar A, Talukder A H, Mandal M, et al. (2002) A naturally occurring MTA1 variant sequesters oestrogen receptor-alpha in the cytoplasm. Nature 418: 654-657.
38. Moon H E, Cheon H, Lee M S (2007) Metastasis-associated protein 1 inhibits p53-induced apoptosis. Oncol Rep 18: 1311-1314.
39. Li D Q, Pakala S B, Reddy S D, Ohshiro K, Penn S H, et al. (2010) Revelation of p53-independent function of MTA1 in DNA damage response via modulation of the p21 WAF1-proliferating cell nuclear antigen pathway. J Biol Chem 285: 10044-10052.
40. Yoo Y G, Kong G, Lee M O (2006) Metastasis-associated protein 1 enhances stability of hypoxia-inducible factor-1alpha protein by recruiting histone deacetylase 1. EMBO J 25: 1231-1241.
41. Dewhirst M W, Cao Y, Li C Y, Moeller B (2007) Exploring the role of HIF-1 in early angiogenesis and response to radiotherapy. Radiother Oncol 83: 249-255.
42. Semenza G L (2011) Oxygen Sensing, Homeostasis, and Disease REPLY. New England Journal of Medicine 365: 1846-1846.
43. Liu T, Yang M, Yang S, Ge T, Gu L, et al. (2013) Metastasis-associated protein 1 is a novel marker predicting survival and lymph nodes metastasis in cervical cancer. Hum Pathol 44: 2275-2281.
44. Li Y, Chao Y, Fang Y, Wang J, Wang M, et al. (2013) MTA1 promotes the invasion and migration of non-small cell lung cancer cells by downregulating miR-125b. J Exp Clin Cancer Res 32: 33.
45. Tuncay Cagatay S, Cimen I, Savas B, Banerjee S (2013) MTA-1 expression is associated with metastasis and epithelial to mesenchymal transition in colorectal cancer cells. Tumour Biol 34: 1189-1204.
46. Stoladinovic A, Hooke J A, Shriver C D, Nissan A, Kovatich A J, et al. (2007) HYOU1/Orp150 expression in breast cancer. Med Sci Monit 13: BR231-239.
47. Tsukamoto Y, Kuwabara K, Hirota S, Kawano K, Yoshikawa K, et al. (1998) Expression of the 150-kd oxygen-regulated protein in human breast cancer. Lab Invest 78: 699-706.
48. Ozawa K, Tsukamoto Y, Hori O, Kitao Y, Yanagi H, et al. (2001) Regulation of tumor angiogenesis by oxygen-regulated protein 150, an inducible endoplasmic reticulum chaperone. Cancer Res 61: 4206-4213.
49. Kinoshita T, Nohata N, Watanabe-Takano H, Yoshino H, Hidaka H, et al. (2012) Actin-related protein 2/3 complex subunit 5 (ARPC5) contributes to cell migration and invasion and is directly regulated by tumor-suppressive microRNA-133a in head and neck squamous cell carcinoma. Int J Oncol 40: 1770-1778.
50. Choi J, Hwang Y K, Sung K W, Kim D H, Yoo K H, et al. (2006) Aven overexpression: association with poor prognosis in childhood acute lymphoblastic leukemia. Leuk Res 30: 1019-1025.
51. Herr I, Debatin K M (2001) Cellular stress response and apoptosis in cancer therapy. Blood 98: 2603-2614.
52. Welch M D, DePace A H, Verma S, Iwamatsu A, Mitchison T J (1997) The human Arp2/3 complex is composed of evolutionarily conserved subunits and is localized to cellular regions of dynamic actin filament assembly. J Cell Biol 138: 375-384.
53. Fulda S (2010) Evasion of apoptosis as a cellular stress response in cancer. Int J Cell Biol 2010: 370835.
54. Altieri D C (2004) Coupling apoptosis resistance to the cellular stress response: the IAP-Hsp90 connection in cancer. Cell Cycle 3: 255-256.

We claim:

1. A method of predicting locally advanced breast cancer (LABC) treatment response comprising:
    a) obtaining a biopsy sample from a patient with LABC,
    b) quantifying a gene expression level consisting of a SULT1A1, a SULT1A2, and a PARP6 biomarker in the biopsy sample using an assay selected from the group consisting of Polymerase Chain Reaction, Real Time Polymerase Chain Reaction, Real-time quantitative RT-PCR, Northern blot analysis, in situ hybridization, probe array, or any combination thereof,
    c) quantifying a gene expression level consisting of a SULT1A1, a SULT1A2, and a PARP6 biomarker in a reference control sample using an assay selected from the group consisting of Polymerase Chain Reaction, Real Time Polymerase Chain Reaction, Real-time quantitative RT-PCR, Northern blot analysis, in situ hybridization, probe array, or any combination thereof,
    d) performing DCE-MRI on the subject,
    e) performing a measurement of DCE-MRI enhancement pattern from step (d), and
    f) diagnosing the subject as having an increased chance of benefiting from a chemotherapeutic treatment if the gene expression levels of the SULT1A1, SULT1A2, and PARP6 biomarkers is higher in the biopsy sample as compared to the reference control and the subject exhibits a centripetal (CP) enhancement pattern as measured by the DCE-MRI.

2. The method of claim 1, wherein the subject is a mammal.

3. The method of claim 1, wherein the subject is a human.

4. The method of claim 1, further comprising administering the chemotherapeutic treatment to the subject.

5. A method of predicting locally advanced breast cancer (LABC) treatment response comprising:
    a) obtaining a biopsy sample from a patient with LABC,
    b) quantifying a gene expression level consisting of a MTA1 biomarker in the biopsy sample using an assay selected from the group consisting of Polymerase Chain Reaction, Real Time Polymerase Chain Reaction, Real-time quantitative RT-PCR, Northern blot analysis, in situ hybridization, probe array, or any combination thereof, c) quantifying a gene expression level consisting of a MTA1 biomarker in a reference control sample using an assay selected from the group consisting of Polymerase Chain Reaction, Real Time Polymerase Chain Reaction, Real-time quantitative RT-PCR, Northern blot analysis, in situ hybridization, probe array, or any combination thereof, d) performing DCE-MRI on the subject, e) performing a measurement of DCE-MRI enhancement pattern from step (d), and f) diagnosing the subject as having an increased chance of benefiting from a chemotherapeutic treatment if the gene expression levels of the MTA1 biomarkers is higher in the biopsy sample as compared to the reference control and the subject exhibits a centrifugal (CF) enhancement pattern as measured by the DCE-MRI.

6. The method of claim 5, wherein the subject is a mammal.

7. The method of claim 5, wherein the subject is a human.

8. The method of claim 5, further comprising administering the chemotherapeutic treatment to the subject.

* * * * *